United States Patent [19]

Nakashima

[11] Patent Number: 5,580,943
[45] Date of Patent: Dec. 3, 1996

[54] IMIDAZOLINYL-FUNCTIONAL ORGANOSILOXANES AND METHOD FOR PREPARATION THEREOF

[75] Inventor: Hisataka Nakashima, Fukuoka Prefecture, Japan

[73] Assignee: Dow Corning Toray Silicone Co., Ltd., Tokyo, Japan

[21] Appl. No.: 535,393

[22] Filed: Sep. 28, 1995

[30] Foreign Application Priority Data

Sep. 30, 1994 [JP] Japan .................................. 6-261954

[51] Int. Cl.$^6$ .................................................. C08G 77/26
[52] U.S. Cl. .............................. 528/26; 528/38; 548/110; 548/347.1; 556/413
[58] Field of Search ........................ 528/26, 38; 548/110, 548/347.1; 556/413

[56] References Cited

U.S. PATENT DOCUMENTS

| | | | |
|---|---|---|---|
| 3,373,137 | 3/1968 | Saam | 260/46.5 |
| 3,408,361 | 10/1968 | Mannheimer | 260/309.6 |
| 3,440,261 | 4/1969 | Saam | 260/448.2 |
| 4,028,343 | 6/1977 | Amort et al. | 260/59 R |
| 4,467,063 | 8/1984 | Lockhart | 524/106 |
| 4,507,455 | 3/1985 | Tangney et al. | 528/26 |
| 4,604,443 | 8/1986 | Chang et al. | 528/28 |
| 4,797,439 | 1/1989 | Peccoux | 524/188 |
| 4,891,166 | 1/1990 | Schaefer et al. | 260/404.5 |
| 4,918,140 | 4/1990 | Peccoux et al. | 524/860 |
| 5,084,577 | 1/1992 | Bolich, Jr. | 548/110 |

Primary Examiner—Margaret W. Glass
Attorney, Agent, or Firm—Roger H. Borrousch

[57] ABSTRACT

Imidazolinyl-functional organosiloxanes in which an aliphatically unsaturated monovalent hydrocarbon radical is bonded at the 2-position of the imidazoline ring, have from 2 to 1,100 siloxane units where at least one siloxane unit has an imidazolinyl radical of the following general formula bonded to silicon

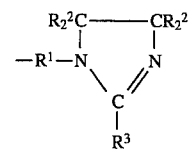

wherein $R^1$ is a $C_1$ to $C_{50}$ divalent hydrocarbon radical, each $R^2$ is hydrogen atom or a $C_1$ to $C_{50}$ monovalent hydrocarbon radicals, and $R^3$ is a $C_2$ to $C_{50}$ aliphatically unsaturated monovalent hydrocarbon radical, and method for the preparation thereof by a dehydration reaction of an amino-functional organosiloxane and an aliphatically unsaturated monocarboxylic acid.

8 Claims, 6 Drawing Sheets

IMIDAZOLINYL-FUNCTIONAL ORGANOSILOXANES AND METHOD FOR PREPARATION THEREOF

BACKGROUND OF THE INVENTION

1. Field of the Invention

This invention relates to novel imidazolinyl-functional organosiloxanes and to a method for the preparation thereof. More particularly, this invention relates to imidazolinyl-functional organosiloxanes that carry an imidazolinyl radical substituted by an aliphatically unsaturated monovalent hydrocarbon radical at the 2 position of the imidazoline ring. These novel imidazolinyl-functional organosiloxanes are useful as additives for modifying the surfaces of the cured products from room-temperature-curable (RTV) organopolysiloxane compositions. This invention also relates to a method for the preparation of subject imidazolinyl-functional organosiloxanes.

2. Background Information

Description of the Prior Art

Organosiloxanes containing an imidazolinyl radical such as that of the following formula $$\begin{array}{c} H_2C \text{———} CH_2 \\ | \quad\quad\quad | \\ -CH_2CHCH_2-N \quad\quad N \\ | \quad\quad\quad\quad \diagdown C \diagup \\ CH_3 \quad\quad\quad\quad || \\ \quad\quad\quad\quad\quad H \end{array}$$

in the molecule where the nitrogen atom bonded to the $$\begin{array}{c} -CH_2CHCH_2- \\ | \\ CH_3 \end{array}$$

radical is the 1-position, the carbon atom bonded to hydrogen atom and the double bond is the 2-position, the nitrogen atom bonded to the double bond is the 3-position, and going in a counter clockwise direction the remaining carbon atoms are the 4-position and the 5-position are known from U.S. Pat. No. 3,373,137, issued Mar. 12, 1968, to Saam (equivalent to Japanese Patent Publication Sho 42-1039) and from U.S. Pat. No. 4,797,439, issued Jan. 10, 1989, to Peccaux (equivalent to Japanese Patent Application Laid Open [Kokai or Unexamined] Number Sho 63-75062). Organosiloxanes containing imidazolinyl-functional radicals with monovalent hydrocarbon radicals which are free of aliphatic unsaturation substituted in the 2-position are known from U.S. Pat. No. 3,440,261, issued Apr. 22, 1989, to Saam. However, imidazolinyl-functional organosiloxane in which the 2-position of the imidazoline ring is substituted by an aliphatically unsaturated monovalent hydrocarbon radical is unknown.

Problems to Be Solved by the Invention

The inventor achieved the instant invention as the result of extensive investigations directed to the development of imidazolinyl-functional organosiloxanes in which the 2 position of the imidazoline ring is substituted by an unsaturated hydrocarbon radical.

SUMMARY OF THE INVENTION

In specific terms, the present invention takes as its object novel imidazolinyl-functional organosiloxanes in which an aliphatically unsaturated monovalent hydrocarbon radical is bonded at the 2-position of the imidazoline ring. Another object of the present invention is a method for the preparation of these novel imidazolinyl-functional organosiloxanes.

Means Solving the Problems and Function Thereof

The present invention relates to an imidazolinyl-functional organosiloxane comprising from 2 to 1,100 siloxane units where at least one siloxane unit has an imidazolinyl radical of the following general formula bonded to silicon $$\begin{array}{c} R_2^2C \text{———} CR_2^2 \\ | \quad\quad\quad | \\ -R^1-N \quad\quad N \\ \quad\quad \diagdown C \diagup \\ \quad\quad\quad | \\ \quad\quad\quad R^3 \end{array}$$

wherein $R^1$ is a $C_1$ to $C_{50}$ divalent hydrocarbon radical, each $R^2$ is selected from the group consisting of hydrogen atom and a $C_1$ to $C_{50}$ monovalent hydrocarbon radical, and $R^3$ is a $C_2$ to $C_{50}$ monovalent hydrocarbon radical with aliphatic unsaturation.

DESCRIPTION OF THE PREFERRED EMBODIMENTS

The imidazolinyl-functional organosiloxanes according to the present invention contains from 2 to 1,100 siloxane units where at least one siloxane unit has a imidazolinyl radical with the following general formula bonded to silicon.

$$\begin{array}{c} R_2^2C \text{———} CR_2^2 \\ | \quad\quad\quad | \\ -R^1-N \quad\quad N \\ \quad\quad \diagdown C \diagup \\ \quad\quad\quad | \\ \quad\quad\quad R^3 \end{array}$$

The radical $R^1$ is a $C_1$ to $C_{50}$ divalent hydrocarbon radical and is specifically exemplified by alkylene radicals such as methylene, ethylene, propylene, butylene, and so forth, and by arylene radicals such as phenylene, tolylene, xylylene, and so forth. $R^1$ is preferably a $C_1$ to $C_8$ divalent hydrocarbon radical. Each of the radicals $R^2$ is hydrogen atom or an independently selected from $C_1$ to $C_{50}$ monovalent hydrocarbon radicals which are specifically exemplified by methyl, ethyl, and propyl. $R^2$ is preferably hydrogen or a $C_1$ to $C_8$ monovalent hydrocarbon radical. $R^3$ is a $C_2$ to $C_{50}$ aliphatically unsaturated monovalent hydrocarbon radical and is specifically exemplified by vinyl, allyl, butenyl, heptadecenyl, and heptadecadienyl. $R^3$ is preferably a $C_{10}$ to $C_{20}$ monovalent hydrocarbon radical and organosiloxanes where $R^3$ is a mixture of such $C_{10}$ to $C_{20}$ monovalent hydrocarbon radicals is most preferred. Subject imidazolinyl-functional organosiloxane is specifically exemplified by straight-chain organosiloxane with the general formula and by cyclic organosiloxane with the general formula wherein $R^1$, $R^2$, and $R^3$ are each defined as above. Each $R^4$ is independently selected from $C_1$ to $C_{50}$ monovalent hydrocarbon radicals, as specifically exemplified by alkyl radicals such as methyl, ethyl, propyl, etc, and by aryl radicals such as phenyl, tolyl, xylyl, etc. $R^4$ is preferably a $C_1$ to $C_8$ monovalent hydrocarbon radical. Each $R^5$ is the hydroxyl radical or an independent selection from $C_1$ to $C_{50}$ monovalent hydrocarbon radicals wherein said monovalent hydrocarbon radicals are specifically exemplified by alkyl radicals such as methyl, ethyl, propyl, and so forth; by alkenyl radicals such as vinyl, allyl, butenyl, and so forth; and by aryl radicals such as phenyl, tolyl, xylyl, and so forth. $R^5$ is preferably hydroxyl radical or a $C_1$ to $C_8$ monovalent hydrocarbon radical. With regard to the subscripts, a and c each have values from 0 to 1,000, b and d each have values from 1 to 100, and c+d is from 3 to 1,100. The preferred cyclic organosiloxanes are those in which c is from 0 to 30, d is from 3 to 30, and c+d is from 3 to 33.

The imidazolinyl-functional organosiloxanes are specifically exemplified by organosiloxanes with the following formulas:

The method for preparing the above-described imidazolinyl-functional organosiloxanes is a dehydration reaction between (A) an amino-functional organosiloxane and (B) an aliphatically unsaturated monocarboxylic acid.

For example, straight chain imidazolinyl-functional organosiloxanes can use as the starting siloxane, (A) an amino-functional organosiloxane of the general formula and cyclic imidazolinyl-functional organosiloxanes can use as the starting siloxanes, (A) a cyclic amino-functional organo-siloxane with the general formula in the preparative method. In the preceding formulas $R^1$, $R^2$, $R^4$, $R^5$, a, b, c, and d are defined as describe above. Subject amino-functional organosiloxanes can be synthesized, for example, by the alkali-catalyzed equilibration polymerization of such precursors as amino-functional cyclosiloxane and organocyclosiloxane using endblockers such as water and hexaalkyldisiloxane where endblocking is desired.

Amino-functional organosiloxanes of (A) encompass organosiloxanes exemplified by the following formulas:

The carboxylic acid used as component (B) has the general formula $R^3COOH$, wherein $R^3$ is a $C_2$ to $C_{50}$ aliphatically unsaturated monovalent hydrocarbon radical as specifically exemplified by vinyl, allyl, butenyl, heptadecenyl, and heptadecadienyl. Subject carboxylic acid is itself specifically exemplified by acrylic acid, methacrylic acid, oleic acid, linoleic acid, linolenic acid, and ricinoleic acid, by drying oil fatty acids as obtained by the hydrolysis of a drying oil may be directly used as component (B), and said drying oil fatty acids are exemplified by soybean oil fatty acids, dehydrated castor oil fatty acids, tall oil fatty acids, linseed oil fatty acids, and tung oil fatty acids. The drying oil fatty acids are mixtures of carboxylic acids having the formula $R^3COOH$ and may also contain some saturated carboxylic acids as found in such drying oil hydrolysis products. The use of drying oil fatty acids is preferred when the imidazolinyl-functional organosiloxane according to the present invention is to be used as an additive for modifying the surface of cured products from RTV organopolysiloxane compositions.

The imidazolinyl-functional organosiloxanes are obtained by a dehydration reaction between components (A) and (B). Straight-chain amino-functional organosiloxanes are used as component (A) when straight-chain imidazolinyl-functional organosiloxanes are desired. Cyclic amino-functional organosiloxanes are used as component (A) when cyclic imidazolinyl-functional organosiloxanes are used. The mixing ratio of components (A) and (B) in this preparative method is preferably 0.5 mole component (B) per 1 mole amino group in component (A). Unreacted component (A) will remain when component (B) is used at less than 0.5 mole per 1 mole amino group in component (A), while unreacted component (B) will remain when component (B) is used at more than 0.5 mole per 1 mole amino group in component (A).

The reaction temperature is preferably in the range from 100° C. to 300° C. and more preferably in the range from 150° C. to 250° C. The dehydration reaction does not go to completion at a reaction temperature below 100° C., which prevents synthesis of the imidazolinyl-functional organosiloxane. Undesirable secondary reactions become a possibility at temperatures in excess of 300° C. Organic solvent and dehydrating reagent may be used in this preparative method insofar as the object of the present invention is not impaired. Toluene and xylene, which are already known for azeotropic dehydration, are advantageously used as an organic solvent, and should be used in an amount that gives a reaction temperature in the range specified above. The dehydrating reagent is exemplified by molecular sieves and dicyclohexylcarbodiimide.

Because imidazolinyl-functional organosiloxanes are miscible with organopolysiloxane used to make RTV organopolysiloxane compositions, it is useful as an additive for improving the physical properties of room-temperature-curable organopolysiloxane compositions and particularly as an additive for improving the surface of the cured products obtained from room-temperature-curable organopolysiloxane compositions. The aliphatic unsaturation of $R^3$ in the imidazolinyl radical provides the anti-staining property of an RTV silicone composition containing it as an additive. This anti-staining property is believed to be based on the ease of oxidation and hydrolytic cleavage attributed to $R^3$ which provides hydrophilicity to the surface of cured RTV silicone sealant composition. This hydrophilicity is achieved by the hydrolytic cleavage of the oxidized aliphatically unsaturated monovalent hydrocarbon radical $R^3$. Whereas if a saturated monovalent hydrocarbon radical were to replace $R^3$ and such a imidazolinyl functional organosiloxane were to be used as an additive to an RTV silicone sealant composition, a hydrophilic surface would not be formed on the resulting cured RTV silicone sealant surface and a self-cleaning and anti-staining property would not be observed.

The invention will be explained in greater detail in the following examples which are presented for illustrative purposes and should not be construed as limiting the invention which is properly delineated in the claims.

EXAMPLE 1

While operating under a dry nitrogen current, 249.9 g of straight-chain amino-functional organosiloxane with the formula (amino value as NH=0.89 weight %)

and 37.1 g xylene were introduced into a 1-L flask equipped with stirrer, thermometer, and water-measurement tube fitted with a reflux condenser and were stirred. The resulting mixture was then heated to reflux at 160° C. Separately, 20.7 g mixed fatty acid, Hy-Diene, containing about 58 weight percent of conjugated linoleic acid, 27 weight percent non-conjugated linoleic acid, 7 weight percent oleic acid, 5 weight percent ricinoleic acid, 1 weight percent palmitic acid, and 2 weight percent stearic acid (neutralization value= 198.3, brand name: Hy-Diene from KF Trading Company, Tokyo, Japan) was weighed into an addition funnel, which was then installed on the 1-L flask. This mixed fatty acid was subsequently added dropwise over 1.3 hours at 160° C. into the mixture of amino-functional organosiloxane and xylene. After the completion of this addition, the dehydration reaction was completed by stirring for 4.6 hours at 160° C. to 179° C., after which interval 2.0 mL water had distilled into the water-measurement tube. The resulting reaction mixture was then cooled to room temperature, combined with 20 g filtration aid (brand name: Radiolite 900 from Showa Kagaku Kogyo Kabushiki Kaisha, Tokyo, Japan) and 146.3 g toluene, stirred for 30 minutes, and finally subjected to fine filtration. After filtration, the solvent in the filtrate was stripped off at 70° C./30 mmHg for 1 hour and then at 72° C./8 mmHg to 80° C./10 mmHg for 4 hours to give 238.9 g of a straight-chain imidazolinyl-functional organosiloxane of the following formula:

The —$C_{17}H_{31}$ radical shown in the above formula represents the reacted residue from the Hy-diene acid mixture as determined from the molecular weight.

Figure 1:
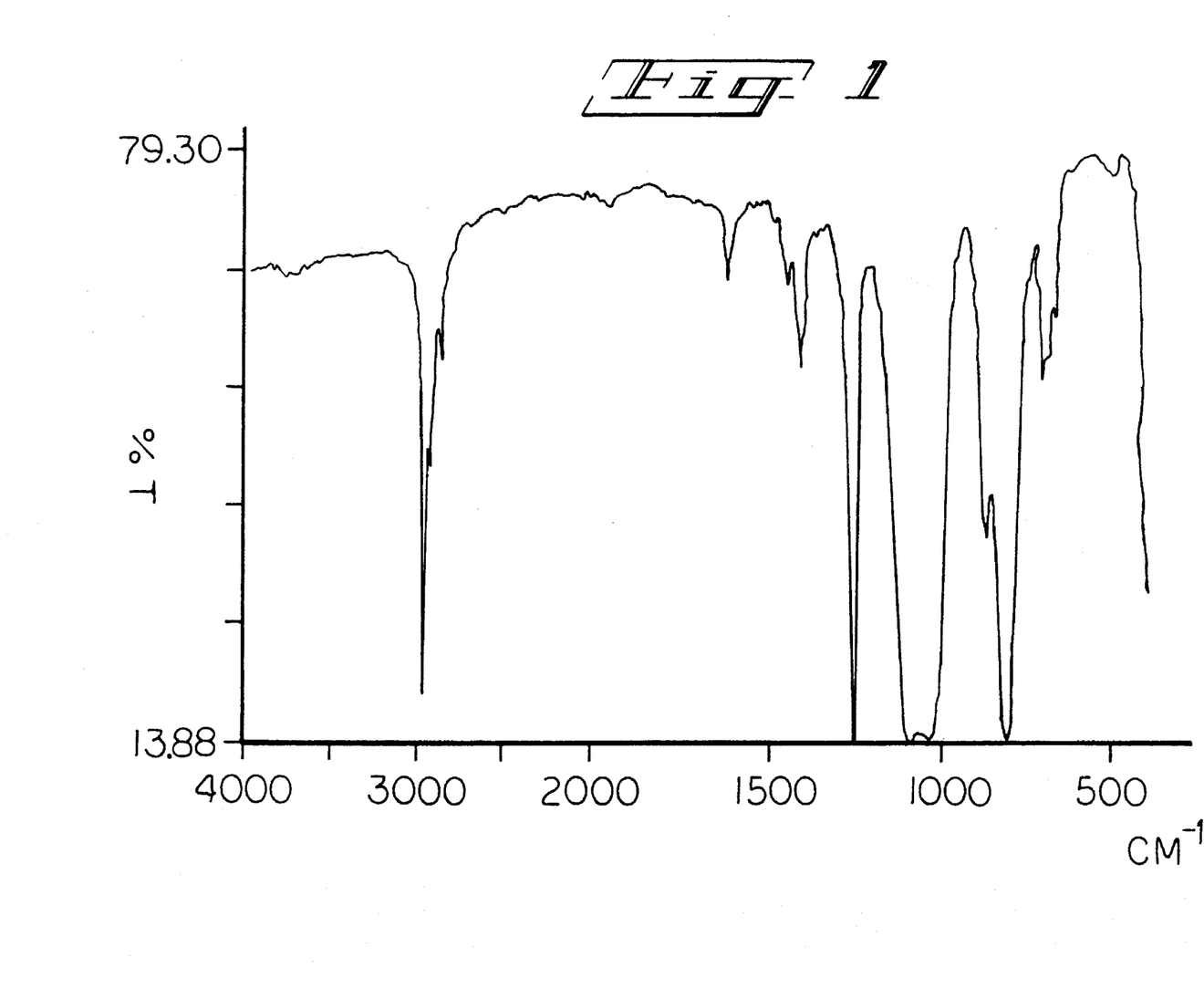
FIG. 1 is a chart of the infrared absorption spectrum of the imidazolinyl-functional organosiloxane obtained in Example 1.
Figure 2:
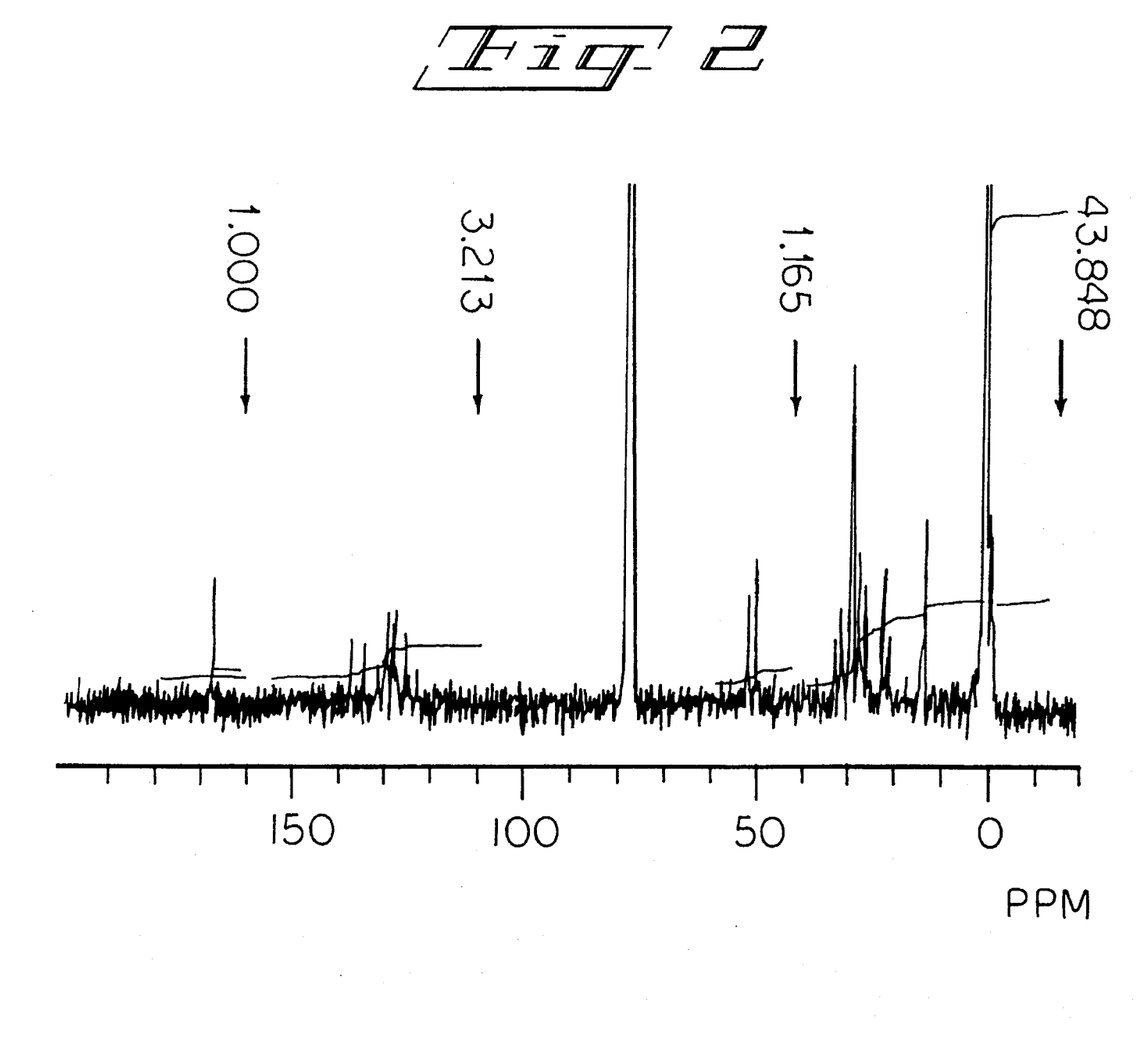
FIG. 2 is a chart of the $^{13}$C-nuclear magnetic resonance spectrum of the imidazolinyl-functional organosiloxane obtained in Example 1.

Analysis of this organosiloxane by $^{13}$C-nuclear magnetic resonance analysis ($^{13}$C-NMR) confirmed the presence of the signal for the imino group carbon in the imidazoline ring at 167.1 ppm, see FIG. 2. Analysis of this organosiloxane by infrared absorption spectroscopy confirmed the presence of the imino group signal at 1,620 cm$^{-1}$, see FIG. 1.

EXAMPLE 2

While operating under a dry nitrogen current, 11.6 g straight-chain amino-functional organosiloxane with the formula (amino value as NH=0.89 weight %)

$$(CH_3)_3SiO(\underset{\underset{CH_3}{|}}{\overset{\overset{CH_3}{|}}{Si}}O)_{325.7}(\underset{\underset{C_3H_6NHC_2H_4NH_2}{|}}{\overset{\overset{CH_3}{|}}{Si}}O)_{8.2}Si(CH_3)_3$$

1.68 g soybean oil fatty acid mixture, and 1 g xylene were placed in a 0.5-L flask equipped with stirrer, thermometer, and water-measurement tube fitted with a reflux condenser and were stirred. A dehydration reaction was run by heating for 3 hours under reflux at 144° C. to 155° C., after which interval 0.1 mL water had distilled into the water-measurement tube. The reaction mixture was then cooled to room temperature, combined with 5 g filtration aid (brand name: Radiolite 900 from Showa Kagaku Kogyo Kabushiki Kaisha, Tokyo, Japan) and 10 g toluene, stirred for 30 minutes, and finally subjected to fine filtration. After filtration, the solvent in the filtrate was stripped off at 70° C./30 mmHg for 1 hour and then at 72° C./8 mmHg to 80° C./10 mmHg for 2 hours to give 11.1 g of a straight-chain imidazolinyl-functional organosiloxane with the following formula:

The —$C_{17}H_{31}$ radical shown in the above formula represents the reacted residue from the soybean fatty acid mixture as determined from the molecular weight.

Figure 3:
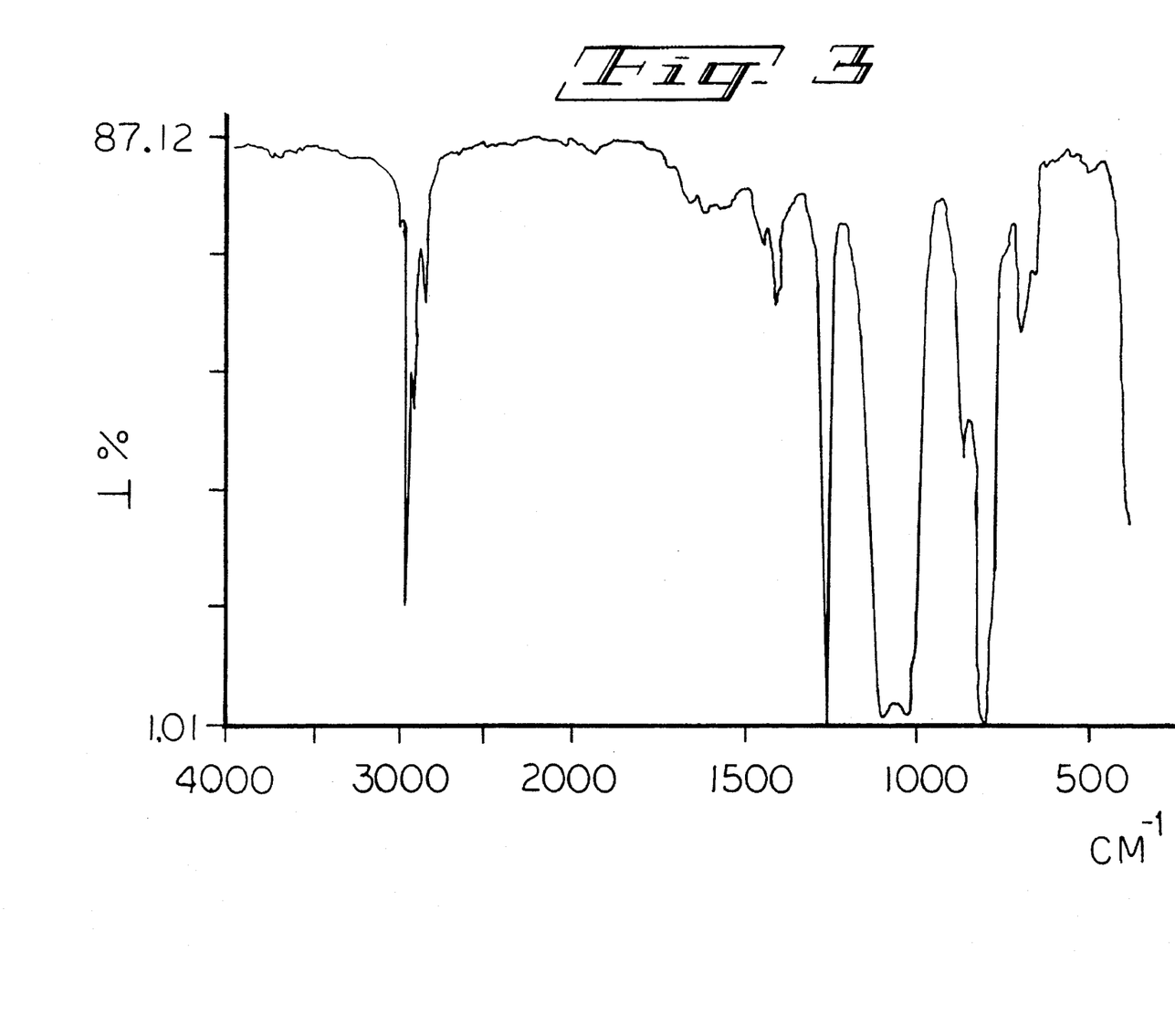
FIG. 3 is a chart of the infrared absorption spectrum of the imidazolinyl-functional organosiloxane obtained in Example 2.
Figure 4:
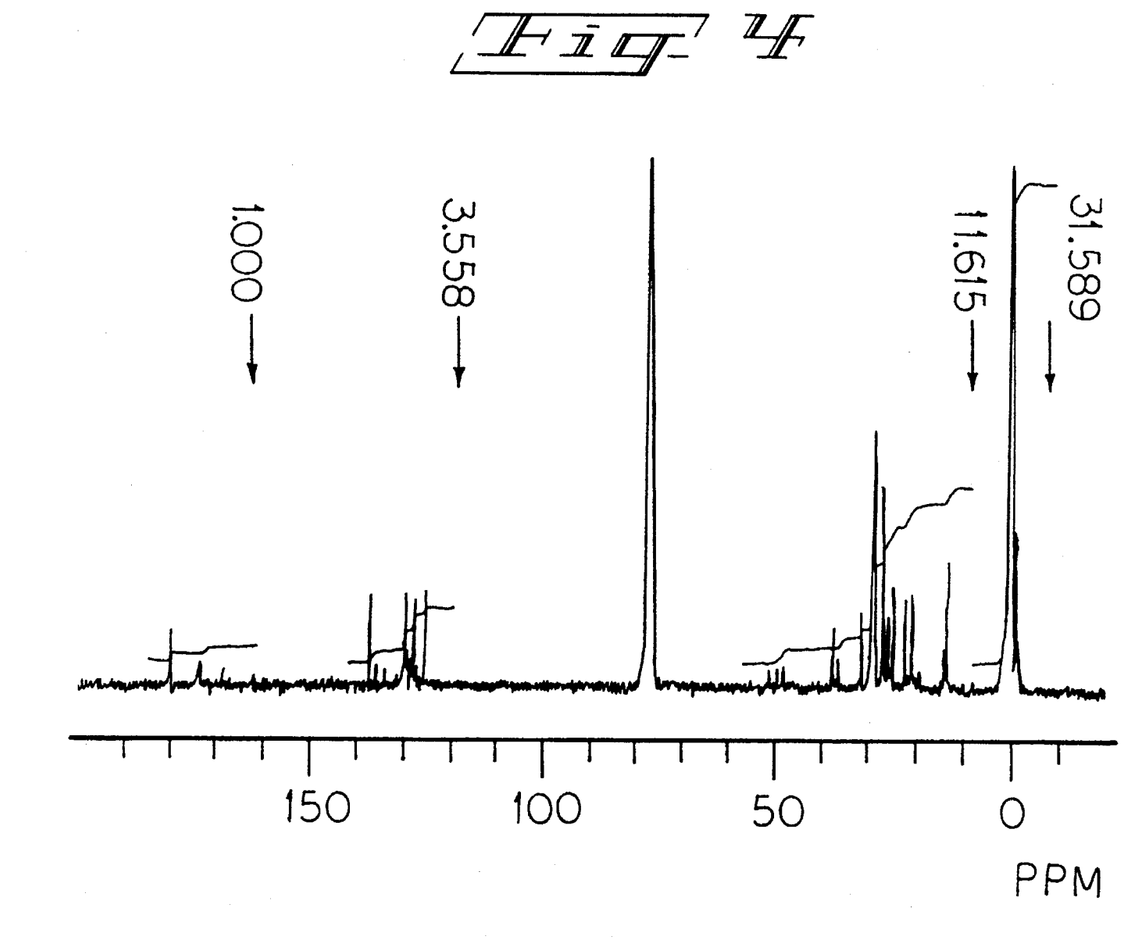
FIG. 4 is a chart of the $^{13}$C-nuclear magnetic resonance spectrum of the imidazolinyl-functional organosiloxane obtained in Example 2.

Analysis of the obtained organosiloxane by $^{13}$C-NMR confirmed the presence of the signal for the imino group carbon in the imidazoline ring at 168 ppm, see FIG. 4. Analysis of the obtained organosiloxane by infrared absorption spectroscopy confirmed the presence of the imino group signal at 1,610 cm$^{-1}$, see FIG. 3.

EXAMPLE 3

Figure 5:
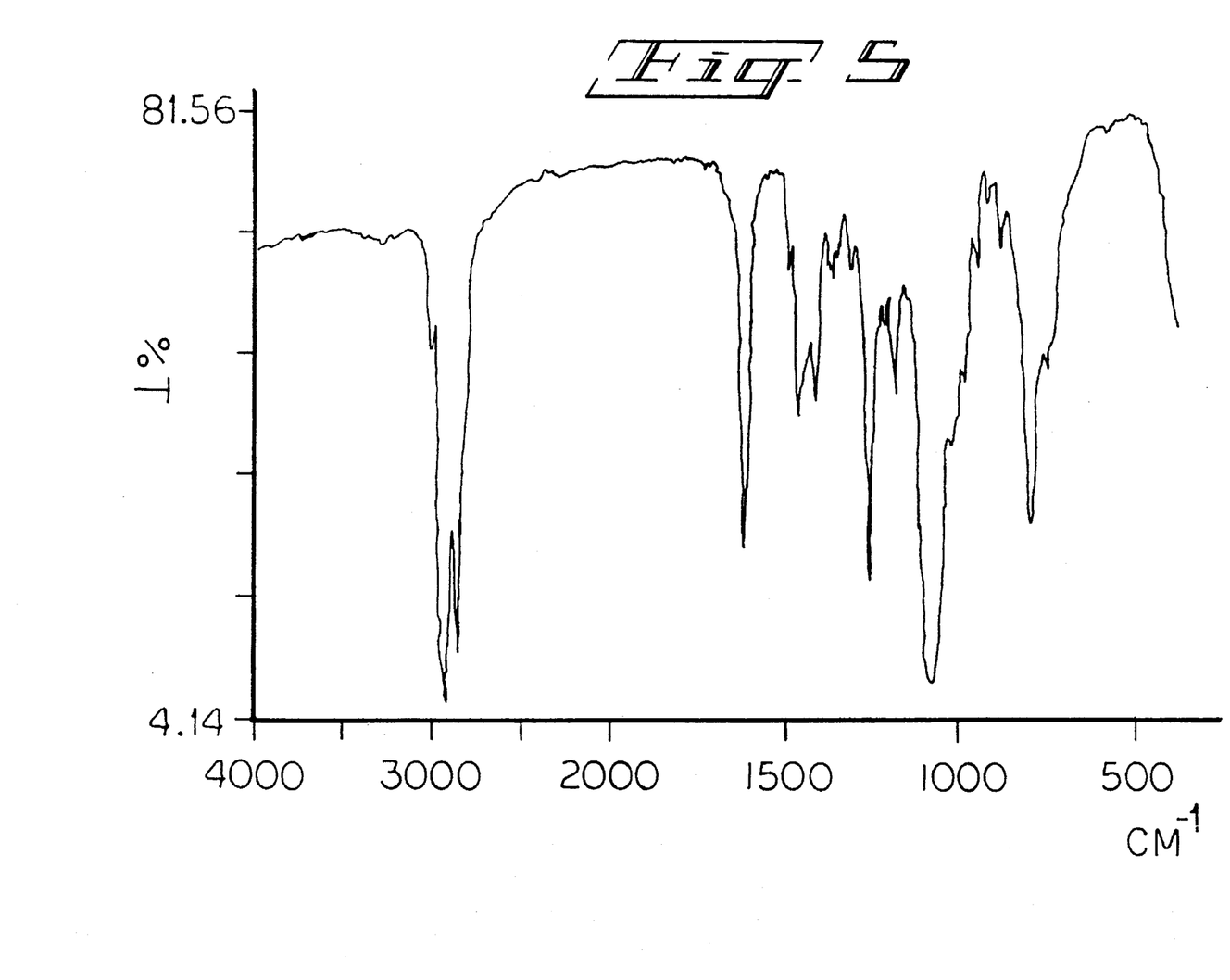
FIG. 5 is a chart of the infrared absorption spectrum of the imidazolinyl-functional organosiloxane obtained in Example 3.
Figure 6:
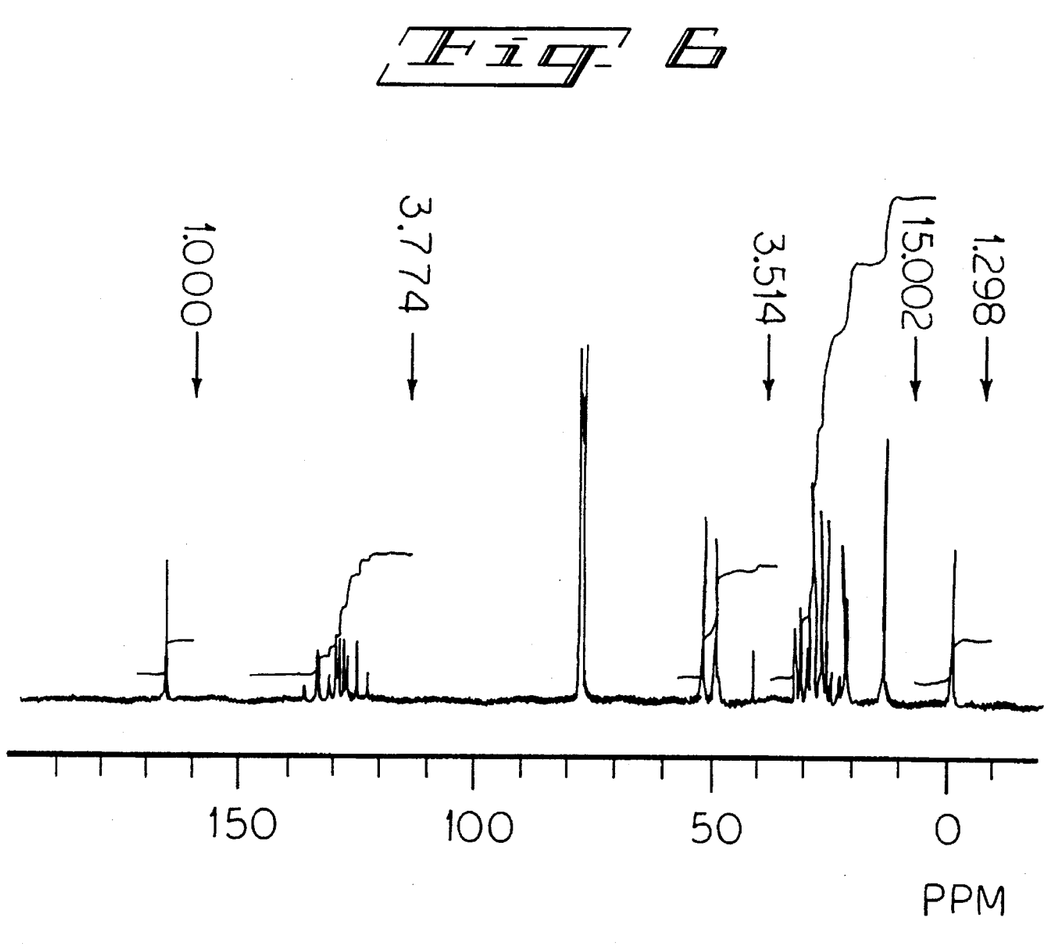
FIG. 6 is a chart of the $^{13}$C-nuclear magnetic resonance spectrum of the imidazolinyl-functional organosiloxane obtained in Example 3.

While operating under a dry nitrogen current, 103.8 g cyclic amino-functional organosiloxane of the formula (amino value as NH=18.2 weight %)

and 41.5 g xylene were introduced into a 0.3-L flask equipped with stirrer, thermometer, and water-measurement tube fitted with a reflux condenser and were stirred. The resulting mixture was then heated to reflux at 145° C. Separately, 140.9 g mixed fatty acid Hy-Diene (neutralization value=198.3, brand name: Hy-Diene from KF Trading Company, Tokyo, Japan) was weighed into an addition funnel, which was then installed on the 0.3-L flask. This mixed fatty acid was subsequently added dropwise over 2.2 hours at 145° C. to 154° C. into the mixture of cyclic amino-functional organosiloxane and xylene. After the completion of this addition, the dehydration reaction was completed by stirring for 5.3 hours at 154° C. to 190° C., after which interval 18.0 mL water had distilled into the water-measurement tube. The resulting reaction mixture was then cooled to room temperature, combined with 20 g filtration aid (brand name: Radiolite 900 from Showa Kagaku Kogyo Kabushiki Kaisha, Tokyo, Japan) and 122.8 g toluene, stirred for 30 minutes, and finally subjected to fine filtration. After filtration, the solvent in the filtrate was stripped off at 70° C./30 mmHg for 1.5 hours and then at 70° C./8 mmHg–80° C./10 mmHg for 4 hours to give 207.1 g of a cyclic imidazolinyl-functional organosiloxane with the following formula:

Analysis of this organosiloxane by $^{13}$C-NMR confirmed the presence of the signal for the imino group carbon in the imidazoline ring at 166.1 ppm, see FIG. 6. Analysis of the organosiloxane by infrared absorption spectroscopy confirmed the presence of the imino group signal at 1,610 cm$^{-1}$, see FIG. 5.

APPLICATION EXAMPLE 1

The following were mixed to homogeneity to give a room-temperature-curable organopolysiloxane composition: 15 g of the imidazolinyl-functional organosiloxane prepared in Example 1, 85 g alpha,omega-dihydroxypolydimethylsiloxane with a viscosity at 25° C. of 18 Pa.s, 100 g precipitated calcium carbonate, 0.3 g dibutyltin octoate, 1 g surfactant, and 16.3 g of methyltris(methyl ethyl ketoxime)silane. This organopolysiloxane composition was filled into a joint (joint width=20 mm, joint depth=10 mm) formed by abutting 2 white ceramic boards. Curing at 25° C. for 5 days then yielded a test panel. This test panel was thereafter held outdoors at an inclination of 75° with the joint on the upper side, and the development of staining on the ceramic board in the vicinity of the joint was examined over a 2-month period. Almost no staining was observed even after the 2 months had elapsed. In addition, the room-temperature-curable organopolysiloxane composition itself was held for 3 months at 25° C. and its appearance was then inspected: no separation or sedimentation was observed.

For purposes of comparison, another room-temperature-curable organopolysiloxane composition was prepared as above, but in this case omitting the 15 g imidazolinyl-functional organosiloxane from Example 1. The post-cure behavior of this organopolysiloxane composition was evaluated as above, and in this case staining was observed on the ceramic board after 1 week.

EFFECTS OF THE INVENTION

The imidazolinyl-functional organosiloxanes according to the present invention are novel compounds. The preparative method according to the present invention is a very efficient method for producing these novel imidazolinyl-functional organosiloxanes.

That which is claimed is:

1. An imidazolinyl-functional organosiloxane comprising from 2 to 1,100 siloxane units where at least one siloxane unit has an imidazolinyl radical of the following general formula bonded to silicon wherein $R^1$ is a $C_1$ to $C_{50}$ divalent hydrocarbon radical, each $R^2$ is selected from the group consisting of hydrogen atom and a $C_1$ to $C_{50}$ monovalent hydrocarbon radical, and $R^3$ is a $C_2$ to $C_{50}$ monovalent hydrocarbon radical with aliphatic unsaturation.

2. The imidazolinyl-functional organosiloxane according to claim 1 where the organosiloxane has the following general formula wherein $R^1$, $R^2$, and $R^3$ are as defined in claim 1, each $R^4$ is a $C_1$ $C_{50}$ monovalent hydrocarbon radical, each $R^5$ is selected from the group consisting of hydroxyl radical and a $C_1$ to $C_{50}$ monovalent hydrocarbon radical, a is from 0 to 1,000, and b is from 1 to 100.

3. The imidazolinyl-functional organosiloxane according to claim 2 in which $R^1$ is a $C_1$ to $C_8$ divalent hydrocarbon radical, $R^2$ is hydrogen atom, $R^3$ is a $C_{10}$ to $C_{20}$ monovalent hydrocarbon radical with aliphatic unsaturation or a mixture thereof, $R^4$ is a $C_1$ to $C_8$ monovalent hydrocarbon radical, and $R^5$ is a hydroxyl radical.

4. The imidazolinyl-functional organosiloxane according to claim 2 in which $R^1$ is a $C_1$ to $C_8$ divalent hydrocarbon radical, $R^2$ is hydrogen atom, $R^3$ is a $C_{10}$ to $C_{20}$ monovalent hydrocarbon radical with aliphatic unsaturation or a mixture thereof, $R^4$ is a $C_1$ to $C_8$ monovalent hydrocarbon radical, and $R^5$ is a $C_1$ to $C_8$ monovalent hydrocarbon radical.

5. The imidazolinyl-functional organosiloxane according to claim 4 in which $R^1$ is —$C_3H_6$—, $R^3$ is a mixture of —$C_{17}H_{31}$ radicals, $R^4$ is methyl radical, and $R^5$ is methyl radical.

6. The imidazolinyl-functional organosiloxane according to claim 1 where the siloxane has the following general formula wherein $R^1$, $R^2$, and $R^3$ are as defined in claim 1, each $R^4$ is a $C_1$ to $C_{50}$ monovalent hydrocarbon radical, c is from 0 to 1,000, d is from 1 to 100, and c+d is from 3 to 1,100.

7. The imidazolinyl-functional organosiloxane according to claim 6 in which $R^1$ is a $C_1$ to $C_8$ divalent hydrocarbon radical, $R^2$ is hydrogen atom, $R^3$ is a $C_{10}$ to $C_{20}$ monovalent hydrocarbon radical with aliphatic unsaturation or a mixture thereof, $R^4$ is a $C_1$ to $C_8$ monovalent hydrocarbon radical, c is 0 to 30, d is 3 to 30, and c+d is from 3 to 33.

8. The imidazolinyl-functional organosiloxane according to claim 6 in which $R^1$ is —$C_3H_6$—, $R^3$ is a mixture of —$C_{17}H_{31}$ radicals, and $R^4$ is methyl radical.

* * * * *